United States Patent [19]

Bauer et al.

[11] 4,024,259

[45] May 17, 1977

[54] 3-ANILINO-2,4-DIAZABICYCLO[3.2.1]OCTENES

[75] Inventors: Victor John Bauer, Somerville; Lawrence Leo Martin, Lebanon; Brian John Duffy, Flanders, all of N.J.

[73] Assignee: American Hoechst Corporation, Bridgewater, N.J.

[22] Filed: Jan. 26, 1976

[21] Appl. No.: 652,151

[52] U.S. Cl. .................. 424/251; 260/256.4 H; 260/563 P

[51] Int. Cl.$^2$ .............. C07D 239/70; A61K 31/505

[58] Field of Search ............ 260/256.4 H, 256.4 A; 424/251

[56] References Cited

UNITED STATES PATENTS

| 2,899,434 | 8/1959 | Bloom | 260/256.4 H |
| 3,202,660 | 8/1965 | Zeile et al. | 260/256.4 H |

Primary Examiner—Paul M. Coughlan, Jr.
Attorney, Agent, or Firm—Curtis, Morris & Safford

[57] ABSTRACT

Novel 3-anilino-2,4-diazabicyclo[3.2.1]octenes, physiologically tolerable acid addition salts thereof and method of preparing same are described. These compounds are useful as tranquilizers, diuretics and antihypertensives.

11 Claims, No Drawings

3-ANILINO-2,4-DIAZABICYCLO[3.2.1]OCTENES

This invention relates to novel 2,4-diazabicyclo[3.2.1]octenes and to their physiologically tolerable acid addition salts which are useful as tranquilizers, to methods of treatment with pharmaceutically effective amounts thereof and to pharmaceutical compositions containing such compounds as essential active ingredients. Additionally, compounds of the invention are further useful as diuretic and antihypertensive agents.

To the best of our knowledge, the compounds of this invention have not heretofore been described or suggested. 2-Anilino-1,3-diazacycloalkanes as described by B Loev et al., J. Med. Chem., Vol 18, 90 (1975) to represent a potential class of antihypertensive agents are outside the scope of this invention.

The compounds of the present invention have the formula

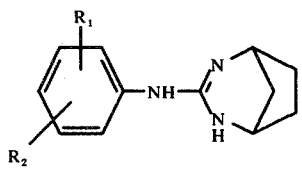

wherein $R^1$ and $R^2$ are the same or different and represent hydrogen, halogen, lower alkoxy, lower alkyl, nitro, or trifluoromethyl. In the above definitions halogen means chlorine, iodine, fluorine and bromine and lower alkyl and lower alkoxy mean those radicals of from 1 to 4 carbon atoms.

Preferred compounds of the invention are those wherein $R^1$ and $R^2$ are the same or different and represent hydrogen, chlorine or fluorine and are on the ortho or para position of the phenyl ring.

Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The compounds of the present invention are produced by the reaction of an imidocarbonyl chloride of the formula

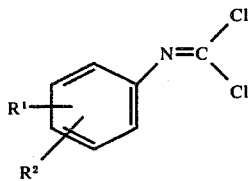

in which $R^1$ and $R^2$ are as defined earlier with cis-1,3-diaminocyclopentane in an organic solvent and at a temperature of from about −75° to 10° C. The hydrogen chloride produced in the reaction can be removed by the presence of an acid scavenger during the reaction or by basifying the reaction solution after the reaction is completed.

Cis-cyclopentane-1,3-diamine dihydrochloride was described by J. D. Roberts et al., JACS, Vol 76, 4501 (1954) as a hygroscopic yellow powder characterized as its dibenzoyl derivative. We have found that by azeotroping with absolute ethanol the dihydrochloride is produced as a colorless, non-hygroscopic crystalline solid. The free base is obtained from the dihydrochloride salt by mixing with two equivalents of powdered sodium hydroxide and distilling the mixture at atmospheric pressure.

An imidocarbonyl chloride is prepared by the addition of a corresponding formanilide to an ice-cold mixture of thionyl chloride and sulfuryl chloride. The mixture is allowed to react at a temperature of from about 0° to 60° C. Alternatively, chlorination of an appropriate phenyl isothiocyanate in a nonpolar organic solvent which is inert under the reaction conditions forms said imidocarbonyl chloride at a temperature of from 0° C. to ambient. A preferred method is carried out with carbon tetrachloride as the solvent and chlorine gas as the chlorinating agent at a temperature of from 5° to 15° C.

The compounds of the present invention are useful as tranquilizers due to their depressant action on the central nervous system of mammals. This activity is demonstrated in the mouse observation procedure, a standard assay for central nervous system depressants [Psychopharmacologia, 9, 259 (1966)]. Thus, for instance, the minimum effective dose (MED) at which 3-(2,6-dichloroanilino)-2,4-diazabicyclo[3.2.1]oct-2-ene, 3-(2-chloroanilino-2,4-diazabicyclo[3.2.1]oct-2-ene, 3-(4-chloroanilino)-2,4-diazabicyclo[3.2.1]oct-2-ene and 3-(4-fluoroanilino)-2,4-diazbicyclo[3.2.1]oct-2-ene display significant effects on behavior and reflex depression together with muscle relaxation is 10 mg/kg of body weight. These data indicate that the compounds are useful as tranquilizers in mammals when administered in amounts ranging from about 1.0 to 100 mg/kg of body weight per day.

Additionally, compounds of the present invention are further useful in mammals as diuretics due to their ability to produce diuresis and as antihypertensives due to their ability to depress blood pressure when administered in amounts ranging from 0.1 to 100 mg/kg of body weight per day.

Further examples of compounds of the invention are:
3-(3,5-dimethoxyanilino)-2,4-diazabicyclo[3.2.1]oct-2-ene;
3-(4-butoxylanilino)-2,4-diazabicyclo[3.2.1]oct-2-ene;
3-(2,6-dimethylanilino)-2,4-diazabicyclo[3.2.1]oct-2-ene;
3-(3-chloro-4-ethylanilino)-2,4-diazabicyclo[3.2.1]oct-2-ene;
3-(4-n-butylanilino)-2,4-diazabicyclo[3.2.1]oct-2-ene; and
3-(4-t-butylanilino)-2,4-diazabicyclo[3.2.1]oct-2-ene.

The active compounds of the present invention may be administered to patients orally, for example, with an inert diluent or with an edible carrier, or enclosed in gelatin capsules, or in the form of compressed tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but this may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

Tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicyclate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain perservatives, dyes, colorings and flavors. Materials used in preparing these various compositions should be pharmaceutically pure and non-toxic in the amounts used.

For the purpose of parenteral therapeutics administration, the active compounds of the invention may be incorporated into a solution or suspension in concentrations of between 0.5 and about 30% of the weight thereof. They should contain at least 0.1% of active compound. The amount of active compound in such compositions should be such that a suitable dosage will be obtained. Preferably, compositions and preparations according to the present invention are prepared so that parenteral dosage units contain between 0.5 to 100 milligrams of active compound.

Solutions or suspensions of the active compounds may also include the following components: a sterile diluent such as water for injection, saline solution, fixed oils, polyethylene glycols, glycerine, propylene glycol or other synthetic solvents; antibacterial agents such as benzyl alcohol or methyl parabens; anti-oxidants such as ascorbic acid or sodium bisulfite; chelating agents such as ethylenediaminetetraacetic acid; buffers such as acetates, citrate or phosphates and agents for the adjustment of tonicity such as sodium chloride or dextrose. Parenteral preparations can be enclosed in ampules, disposable syringes or multiple dose vials made of glass or plastic.

The present invention is further illustrated by the following examples:

EXAMPLE 1

100 ml of concentrated sulfuric acid are added to a mixture of 38.3g of cis-cyclopentane-1,3-dicarboxylic acid and 300 ml of chloroform in a 1 l. three-neck flask supported in a water bath. The water bath is heated to 50° C and 44.5g of sodium azide are added portion wise over a 2 hour span with stirring. After total addition the moisture is stirred for 2 hours at ambient temperature and then cooled to 5° C. 300 ml of water are introduced and the aqueous phase is separated and extracted with chloroform, filtered and any residual chloroform is removed by evaporation under reduced pressure. The aqueous phase is made strongly alkaline with a 50% sodium hydroxide solution and then steam distilled into 30 ml of concentrated hydrochloric acid. The distillate is concentrated under reduced pressure to a small volume and suspended in 500 ml of absolute ethanol. The ethanolic suspension is concentrated and again diluted with 500 ml of absolute ethanol. The precipitate is collected by vacuum filtration and drying at 40° C to give colorless crystals, dec. 240°–260° C, of cis-cyclopentane-1,3-diamine dihydrochloride.

Analysis: Calculated for $C_5H_{12}N_2.2HCl$: 34.69%C; 8.17%H; 40.96%Cl. Found: 34.61%C; 8.23%H; 41.18%Cl.

EXAMPLE 2 a. A mixture of 50 ml of active anhydride and 21.5 ml of 97% formic acid is heated with stirring in the absence of moisture at 50° C for 15 minutes, and then cooled to 5° C. 40.5g of 2,6-dichloroaniline are added portion wise with stirring to the cooled mixture while maintaining the temperature below 10° C. After total addition the resulting suspension is heated at 50° C for 5 hours and then stirred for 16 hours at ambient temperature. The suspension is suction filtered and the filter cake is washed with benzene. The filter cake is recrystallized twice from benzene to give the product, 2,6-dichloroformanilide, mp 175–178° C.

b. 30.0 g of 2,6-dichloroformanilide are added to an ice-cold mixture of 142 g of thionyl chloride and 22.3 g of sulfuryl chloride over a 5 minute span with stirring and in the absence of moisture. The resulting suspension is stirred at 5° C for 40 minutes and then at 50° C for 18 hours, during which time a solution forms. Any residual thionyl and sulfuryl chloride is distilled under reduced pressure to an oil, bp 72°–78° C (0.08 mm), of 2,6-dichlorophenylimidocarbonyl chloride.

By following the procedures described above in steps (a) and (b), the phenylimidocarbonyl chlorides of Example 5 to 8, outlined below, can be prepared.

EXAMPLE 3

142 g of chlorine gas are bubbled into a solution of 135.2 g of phenyl isothiocyanate in 230 ml of carbon tetrachloride at a temperature of between 5° and 15° C over a 4 hour span. The solvent and sulfur dichloride, produced in the reaction, are removed at reduced pressure, leaving an oil which is distilled at 1.0 mm. The fraction distilling at 55°–60° C is a yellow oil of phenylimidocarbonyl chloride.

Analysis: Calculated for $C_7H_5NCl_2$: 48.31%C; 2.89%H; 8.05%N; 40.74%Cl. Found: 47.52%C; 2.82%H; 8.11%N; 39.96%Cl.

By the following procedure described in this example the phenylimidocarbonyl chlorides of Example 4 to 7, outlined below, can also be prepared.

EXAMPLE 4

Solutions of 4.0 g of 2,6-dichlorophenylimidocarbonyl chloride in 12.5 ml of sieve-dried ethyl acetate and 3.3 g of anhydrous cis-1,3-diaminocyclopentane, free base of Example 1, in 12.5 ml of sieve-dried ethyl acetate are added simultaneously with stirring and in the absence of moisture to a chilled mixture of 12.5 ml of anhydrous triethylamine and 10 ml of sieve-dried ethyl acetate. The resultant suspension is stirred for 15 minutes with cooling and then for 16 hours at ambient temperature. The mixture is suction filtered, the filter cake is washed well with ethyl acetate, and the filtrate and washings are combined and evaporated under reduced pressure, leaving a tacky solid which is recrystallized from acetonitrile to give colorless crystals, mp 161–164° C, of 3-(2,6-dichloroanilino)-2,4-diazabicyclo[3.2.1]oct-2-ene.

Analysis: Calculated for $C_{12}H_{13}Cl_2N_3$: 53.34%C; 4.86%H; 26.24%Cl; 15.56%N. Found: 53.26%C; 4.84%H; 26.27%Cl; 15.49%N.

EXAMPLE 5

Solutions of 1.72 g of 2-chlorophenylimidocarbonyl chloride in 10 ml of anhydrous ether and 1.82 g of cis-1,3-diaminocyclopentane, free base of Example 1, in 20 ml of anhydrous ether are added simultaneously and dropwise at −60° C over a 5 minute span to a mixture of 1.6 g of anhydrous sodium carbonate and 10 ml of anhydrous ether. After total addition, the mixture is stirred at −50° C for 2 hours and then at ambient temperature for 16 hours. The mixture is suction filtered and the filter cake is washed well with anhydrous ether and suspended in 50 ml of water. The aqueous suspension is made strongly alkaline with a 50% sodium hydroxide solution and the mixture is extracted with ether. The combined ether extracts are washed well with water, dried and filtered and the ether is removed, leaving a solid. The solid is recrystallized from acetonitrile to give colorless crystals, mp 158°–162° C, of 3-(2-chloroanilino)-2,4-diazbicyclo[3.2.1]oct-2-ene.

Analysis: Calculated for $C_{12}H_{14}ClN_3$: 61.17%C; 5.95%H; 17.84%N. Found: 61.13%C; 5.92%H; 17.60%N.

EXAMPLE 6

Solutions of 1.72 g of 4-chlorophenylimidocarbonyl chloride in 10 ml of anhydrous ether and 1.80 g of cis-1,3-diaminocyclopentane, free base of Example 1, in 20 ml of anhydrous ether are added simultaneously and dropwise with stirring at −60° C over a 5 minute span to 10 ml of anhydrous ether. After total addition, the mixture is stirred for 2 hours at −60° C and then for 16 hours at ambient temperature. The mixture is suction filtered, the filter cake is suspended in 50 ml of water and the aqueous suspension is made strongly alkaline with a 50% sodium hydroxide solution. The mixture is washed with chloroform and filtered. The filtrate is evaporated, leaving a solid which is triturated with acetonitrile and collected by suction filtration. Recrystallization from acetonitrile gives colorless crystals, mp 216°–218° C, of 3-(4-chloroanilino)-2,4-diazabicyclo[3.2.1]oct-2-ene.

Analysis: Calculated for $C_{12}H_{14}ClN_3$: 61.17%C; 5.95%H; 17.84%N. Found: 61.42%C; 5.94%H; 17.69%N.

EXAMPLE 7

Solutions of 1.59 g of 4-fluorophenylimidocarbonyl chloride in 10 ml of anhydrous ether and 1.80 g of cis-1,3-diaminocyclopentane, free base of Example 1, in 20 ml of anhydrous ether are added simultaneously and dropwise over a 12 minute span with stirring at −60° C to 10 ml of anhydrous ether. After total addition, the reaction mixture is stirred for 16 hours during which time the temperature is allowed to reach ambient temperature. The mixture is suction filtered and the filter cake is washed well with ether and suspended in 50 ml of water. The aqueous suspension is made strongly alkaline with a 50% sodium hydroxide solution. The alkaline mixture is extracted with chloroform and the combined extracts are dried and filtered and the chloroform is removed, leaving a solid residue. The residue is suspended in a small quantity of acetonitrile and then collected by suction filtration. Recrystallization from acetonitrile gives cream colored crystals, mp 182°–184° C, of 3-(4-fluoroanilino)-2,4-diazabicyclo[3.2.1]oct-2-ene.

Analysis: Calculated for $C_{12}H_{14}FN_3$: 65.72%C; 6.45%H; 19.17%N. Found: 65.63%C; 6.47%H; 19.18%N.

EXAMPLE 8

Solutions of 3.0 g phenylimidocarbonyl chloride in 15 ml of anhydrous ether and 3.6 g of cis-1,3-diaminocyclopentane, free base of Example 1a, in 15 ml of anhydrous ether are added simultaneously and dropwise over a 15 minute span with stirring at a temperature of −60° C to 25 ml of anhydrous ether. A white precipitate forms immediately and, after total addition, the mixture is stirred for an additional 2 hours at −60° C and then allowed to reach ambient temperature while stirring continues for 16 hours. The precipitate is collected by filtration, washed well with anhydrous ether and dried. The precipitate is suspended in water and the aqueous suspension is made basic by addition of a 50% sodium hydroxide solution. The mixture is extracted with chloroform and the combined chloroform extracts are washed with water, dried and filtered and the chloroform is removed, leaving a solid. The solid is recrystallized successively from acetonitrile and isopropyl alcohol to give a colorless solid, mp 180°–182° C, of 3-anilino-2,4-diazabicyclo[3.2.1]oct-2-ene.

Analysis: Calculated for $C_{12}H_{15}N_3$: 71.61%C; 7.51%H, 20.88%N. Found: 70.73%C; 7.61%H; 20.99%N.

By procedures similar to those in Examples 4–8, the reaction of cis-1,3-diaminocyclopentane with 2,6-diaminocyclopentane with 2,6-dibromophenylimidocarbonyl chloride, 4-methoxyphenylimidocarbonyl chloride, 3-ethylphenylimidocarbonyl chloride, 2-trifluoromethylphenylimidocarbonyl chloride, 3-fluorophenylimidocarbonyl chloride, 4-nitrophenylimidocarbonyl chloride, 2-bromo-6-chlorophenylimidocarbonyl chloride and 3,5-dichlorophenylimidocarbonyl chloride produces 3-(2,6-dibromoanilino)-2,4-diazabicyclo[3.2.1]oct-2-ene, 3-(4-methoxyalinino)-2,4-diazabicyclo[3.2.1]oct-2-ene, 3-(3-ethylanilino)-2,4-diazabicyclo[3.2.1]oct-2-ene, 3-(2-trifluoromethylanilino)-2,4-diazabicyclo[3.2.1]oct-2-ene, 3-(3-fluoroanilino)-2,4-diazabicyclo[3.2.1]oct-2-ene, 3-(4-nitroanilino)-2, 4-diazabicyclo[3.2.1]oct-2-ene, 3-(2-bromo-6-chloranilino)-2, 4-diazabicyclo[3.2.1]oct-2-ene and 3-(3,5-dichloroanilino)-2,4-diazabicyclo[3.2.1]oct-2-ene, respectively.

We claim:

1. A compound of the formula

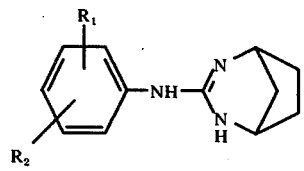

wherein $R^1$ and $R^2$ are the same or different and represent hydrogen, halogen, lower alkoxy, lower alkyl, nitro or trifluoromethyl; or a physiologically tolerable acid addition salt thereof.

2. A compound as defined in claim 1 wherein $R^1$ and $R^2$ are the same or different and represent hydrogen or halogen.

3. A compound as defined in claim 1 wherein $R^1$ and $R^2$ are the same or different and represent hydrogen, chlorine or fluorine and occupy the para and ortho positions or the two ortho positions of the phenyl ring.

4. The compound as defined in claim 1 which is 3-(2,6-dichloroanilino)-2,4-diazabicyclo[3.2.1]oct-2-ene.

5. The compound as defined in claim 1 which is 3-(2-chloroanilino)-2,4-diazabicyclo[3.2.1]oct-2-ene.

6. The compound defined in claim 1 which is 3-(4-chloroanilino)-2,4-diazabicyclo[3.2.1]oct-2-ene.

7. The compound defined in claim 1 which is 3-(4-fluoroanilino)-2,4-diazabicyclo[3.2.1]oct-2-ene.

8. A method of depressing the central nervous system which comprises administering to a patient a pharmaceutically effective amount of a compound defined in claim 1.

9. A method of treating hypertension which comprises administering to a patient a pharmaceutically effective amount of a compound defined in claim 1.

10. A method of promoting diuresis which comprises administering to a patient a pharmaceutically effective amount of a compound defined in claim 1.

11. A pharmaceutical composition which comprises between about 0.5 and about 70 percent by weight of a compound defined in claim 1 as an essential active ingredient, the balance being a pharmaceutically acceptable carrier therefor.

* * * * *